(12) United States Patent
Rizvi et al.

(10) Patent No.: US 6,613,312 B2
(45) Date of Patent: Sep. 2, 2003

(54) ANTIPERSPIRANT PRODUCTS MADE FROM WET-MILLED ANHYDROUS ANTIPERSPIRANT SALTS

(75) Inventors: Riaz Hassan Rizvi, Aurora, IL (US); Rebecca Sue Moen Jenks, Palatine, IL (US)

(73) Assignee: Unilever Home & Personal Care USA, division of Conopco, Inc., Greenwich, CT (US)

( * ) Notice: Subject to any disclaimer, the term of this patent is extended or adjusted under 35 U.S.C. 154(b) by 0 days.

(21) Appl. No.: 09/999,612

(22) Filed: Oct. 24, 2001

(65) Prior Publication Data

US 2002/0071817 A1 Jun. 13, 2002

Related U.S. Application Data

(60) Provisional application No. 60/243,203, filed on Oct. 25, 2000.

(51) Int. Cl.[7] ............................ A61K 7/37; A61K 7/34; A61K 7/38; A61K 7/00
(52) U.S. Cl. ............................ 424/65; 424/66; 424/68; 424/400; 424/401; 424/DIG. 5
(58) Field of Search .......................... 424/65, 400, 401, 424/DIG. 5, 66, 68

(56) References Cited

U.S. PATENT DOCUMENTS

| | | | |
|---|---|---|---|
| 3,887,692 A | 6/1975 | Gilman | 423/462 |
| 3,904,741 A | 9/1975 | Jones et al. | 423/462 |
| 4,202,879 A | 5/1980 | Shelton | 424/66 |
| 5,069,897 A | 12/1991 | Orr | 424/66 |
| 5,531,986 A | 7/1996 | Shevade et al. | 424/68 |
| 5,833,964 A | 11/1998 | Linn et al. | 424/65 |
| 6,428,778 B1 | 8/2002 | Breker et al. | 424/68 |

FOREIGN PATENT DOCUMENTS

| | | |
|---|---|---|
| EP | 1 057 474 | 12/2000 |
| WO | 01/97768 | 12/2001 |

OTHER PUBLICATIONS

European Search Report in an EP application EP 01 30 8985.

*Primary Examiner*—Shelley A. Dodson
(74) *Attorney, Agent, or Firm*—Kevin J. Stein

(57) ABSTRACT

Antiperspirant compositions which comprise:
  a) a wet-milled antiperspirant active material;
  b) a silicone and/or hydrocarbon carrier material; and
  c) a suspending agent or gellant
are described.

20 Claims, No Drawings

ANTIPERSPIRANT PRODUCTS MADE FROM WET-MILLED ANHYDROUS ANTIPERSPIRANT SALTS

This application claims the benefit of U.S. provisional application No. 60/243,203 filed Oct. 25, 2000.

BACKGROUND OF INVENTION

Anhydrous antiperspirant products can assume many forms—for example soft-solids, roll-ons, and solid sticks. In the past, two problems have been associated with such antiperspirant products.

The first problem is one of stability. More specifically, since the antiperspirant active is included in these product forms, as a suspension, the antiperspirant active does have a tendency to settle out of the product. This can cause the product to be physically unstable. In addition, if antiperspirant active concentrates toward the bottom of a package, such as in a soft solid, solid, or roll-on, the consumer can notice a change in product strength as the product is used up. This change from a product that is too weak in its antiperspirant properties to one that is too strong in its antiperspirant properties can be unpleasant for the consumer.

A second problem associated with anhydrous antiperspirant products has been their tendency to leave white marks on the skin and on the clothes of the consumer.

It would be highly desirable to improve the stability of the antiperspirant active within the antiperspirant product. Doing this would enable the production of a product that had lower levels of suspending agents or gellants, and yet the antiperspirant active still would not settle out. Achieving this stability would also allow for the production of antiperspirant products which had a lower tendency to leave white marks on the skin or clothes. Achieving this stability would also allow for the production of a no-shake roll-on. Additionally, suspending agents or gellants can interfere with the antiperspirant active's ability to physically reach the sweat gland. Therefore using less suspending agents and gellants could improve efficacy.

Achieving these benefits is an object of the present invention.

Publications which are relate to this field of invention are as follows:

Product information sheet from Reheis on the Reach AZP-908 gel.

SUMMARY OF THE INVENTION

According to a first aspect of the invention, there is provided an antiperspirant composition that comprises:
 a) a wet-milled antiperspirant active material;
 b) a silicone and/or hydrocarbon carrier material; and
 c) a suspending agent or gellant, other than Al—Mg-hydroxystearate or cylco-methicone and dimethicone cross-polymer.

According to a second aspect of the invention, there is provided a method for improving the stability of an antiperspirant product comprising the use of an antiperspirant composition as described in the first aspect of the invention.

According to a third aspect of the invention, there is provided a method for treating human body odour, comprising the topical application of an antiperspirant composition as described in the first aspect of the invention.

According to a fourth aspect of the invention, there is provided a method for reducing the tendency of antiperspirant products to leave white marks on the skin and on the clothes of the consumer, said method comprising the use of an antiperspirant composition comprising:
 a) a wet-milled antiperspirant active material; and
 b) a silicone and/or hydrocarbon carrier material.

As noted above, stability of the antiperspirant active ingredient in a roll-on, stick or soft solid has been a problem in past formulations. More specifically, the antiperspirant active included in these product forms can have a tendency to settle out of the product, whether during manufacture or storage. It has been found that anhydrous antiperspirant active materials that have been wet-milled provide better product stability than corresponding anhydrous antiperspirant active materials that have been dry-milled.

As noted above, a second problem associated with antiperspirant products has been their tendency to leave white marks on the skin and on the clothes of the consumer. Again, it has been found that anhydrous antiperspirant active materials that have been wet-milled can leave less white marks on skin and clothes than corresponding anhydrous antiperspirant active materials that have been dry-milled.

Because anhydrous antiperspirant active materials that have been wet-milled can produce a more stable finished product than corresponding than anhydrous antiperspirant active materials that have been dry-milled, compositions with wet-milled antiperspirant active materials can be used in the production of a product that has lower levels of suspending agents or gellants, and yet the antiperspirant active still will not settle out. With lower levels of suspending agents or gellants, products can leave less whitening and residue on the skin. Additionally, using less suspending agents or gellants—which can interfere with the active's ability to physically reach the sweat gland—could improve efficacy.

Additional benefits to this active are its manufacturing impact. More specifically, the antiperspirant active that has been wet-milled is available in a liquid form making it potentially easier to transport to and within the production facility. Also, in its liquid form the antiperspirant active has reduced inhalation hazards to compounding staff.

DETAILED DESCRIPTION OF THE INVENTION

As used herein % means weight percent of the total composition unless otherwise specified. As used herein wet-milling means milling or grinding of antiperspirant salt in the presence of a liquid such as a silicone or hydrocarbon oil or ester.

The compositions of the present invention can be made from known ingredients or from ingredients that are analogous to known ingredients. The compositions of the present invention can be made by known methods or by methods that are analogous to known methods.

The antiperspirant compositions claimed in the present invention comprise:
 a) a wet-milled antiperspirant active material;
 b) a silicone and/or hydrocarbon carrier material; and
 c) a suspending agent or structurant.

More specifically, compositions of the invention can contain about 20 to about 50% antiperspirant active material, and preferably 25 to 35% antiperspirant active material.

The silicones used in the compositions of the invention can be non-volatile silicones such as dimethicone or phenyl trimethicone.

The following is a description of the ingredients that can be used in the compositions of the invention.

Antiperspirant Active

It will be understood that the antiperspirant active material that is described below is wet-milled in the compositions of the invention. Wet-milling is done by means that are conventional in the art. Antiperspirant active powders that have been milled in the presence of liquids are referred to in this specification as wet-milled. Antiperspirant active powders that have been milled in the air are referred to in this specification as dry-milled.

The antiperspirant active in the compositions of the invention is present at from about 15 to about 50% and is a particulate material selected from the group consisting of aluminum zirconium complexes, aluminum chlorohydrates, aluminum chlorohydroxide and mixtures thereof. Aluminum zirconium trichloro hydrex-Gly is preferred.

As noted above, the present compositions contain from about 15% to about 50% by weight of a particulate antiperspirant material. These weight percentages are calculated on an anhydrous metal salt basis (exclusive of glycine, the salts of glycine, or other complexing agents). The particulate antiperspirant material preferably has particle sizes ranging from about 1 to about 100 microns, more preferably from about 1 to about 50 microns. They may be in impalpable or microscopic in form and preferably have a high bulk density (e.g. greater than about 0.7 g/cm$^3$). Such materials include, for example, many aluminum or zirconium astringent salts or complexes and are well known in the art.

Any aluminum astringent antiperspirant salt or aluminum and/or zirconium astringent complex in particulate form can be employed herein. Salts useful as astringent antiperspirant salts or as components of astringent complexes include aluminum halides, aluminum hydroxyhalides, zirconyl oxy halides, zirconyl hydroxyhalides and mixtures of these salt materials.

Aluminum salts of this type include aluminum chloride and the aluminum hydroxy halides having the general formula $Al_2(OH)_xQ_y\cdot XH_2O$ where Q is chlorine, bromine, or iodine; x is from about 2 to about 5, and x+y is about 6 and x and y do not need to be integers and where X is from about 1 to about 6. Aluminum salts of this type can be prepared in the manner described more fully in U.S. Pat. No. 3,887,692 to Gilman, U.S. Pat. No. 3,904,741 Jones and Rubino.

The zirconium salts which are useful in the present invention include both zirconium oxy salts and zirconium hydroxyl salts, also referred to as zirconyl hydroxy salts. These compounds may be represented by the following general empirical formula:

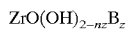

$$ZrO(OH)_{2-nz}B_z$$

wherein z may vary from about 0.9 to about 2 and need not be an integer, n is the valence of B, 2−nz is greater than or equal to 0, and B may be selected from the group consisting of halides, nitrate, sulfamate, sulfate, and mixtures thereof. Although only zirconium and aluminum compounds are exemplified in the specification, it will be understood that other metals such as the Group IV B metals, including hafnium could be used in the present invention.

As with the basic aluminum compounds, it will be understood that the above formula is greatly simplified and is intended to represent and include compounds having coordinated and/or bound water in various quantities as well as polymers, mixtures and complexes of the above. As will be seen from the above formula the zirconium hydroxyl salts actually represent a range of compounds having various amounts of the hydroxyl group, varying from about 1.1 to only slightly greater than 0 groups per molecule.

Several types of antiperspirant complexes using the above antiperspirant salts are known in the art. For example, U.S. Pat. No. 3,792,068 Luedders et al., discloses complexes of aluminum, zirconium and amino acids such as glycines. Complexes such as those disclosed in Luedders and other similar complexes are commonly known as ZAG (OR Zag). ZAG complexes are chemically analyzable for the presence of aluminum, activated ZAG compounds and chlorine. ZAG complexes useful herein are identified by the specification of both the molar ratio of aluminum to zirconium (the Al:Zr ratio) and the molar ratio of total metal to chlorine (metal:Cl) ZAG complexes useful herein have an Al:Zr ratio of from about 1.67 to about 12.5 and a metal:Cl ratio of about 0.73 to about 1.93.

Another patent which discloses ZAG compounds is U.S. Pat. No. 4,985,238 to Tanner et al. Preferred ZAG complexes are described in U.S. Pat. No. 4,985,238 to Tanner et al.

Another patent which discloses activated ZAG compounds (AZAG or AZG compounds) is U.S. Pat. No. 5,486,347 to Callaghan et al. Activated ZAG compounds may be employed as the particulate antiperspirant active in the compositions of the present invention.

Activated ZAG compounds may be prepared by heating an aqueous solution containing an aluminum chlorhydroxide component and mixing it with a zirconium hydroxy chloride component.

Examples of wet-milled actives: S450 Gly or S340 Gly from Giulini (Ludwigshaven, Germany); Reach AZP-908 gel from Reheis, Inc. (Berkeley Heights, N.J.).

Suspending Agent or Gellant

A suspending agent or gellant is used in most aspects of the present invention. The present invention has the advantage of requiring lower levels of such components without sacrificing stability or efficacy (vide supra).

Suitable gellants include waxes, in particular microcrystalline waxes, hydrogenated castor oil, paraffin waxes, alkyl silicone waxes, and synthetic waxes, such as Synchrowax HGL-C. Other suitable gellants are fatty alcohols, in particular those having from 12 to 22 carbon atoms, such as stearyl alcohol (18 carbon atoms), soaps, in particular those having from 12 to 22 carbon atoms, such as sodium stearate (18 carbon atoms), 12-hydroxystearic acid, dibutyl lauroyl glutamine, bibenzylidene sorbitol, and cellulosic materials like hydroxy propyl cellulose and hydroxyethyl cellulose. Gellants are particularly beneficial in solid stick and soft solid compositions and products.

Suitable suspending agents include quaternium-18 bentonite, quaternium-18 hectorite, silica, and propylene carbonate. Quaternium-18 bentonite is particularly preferred. Suspending agents are particularly beneficial in roll-on compositions and products.

Deodorant Active

A deodorant active may be used in the compositions of the invention in an amount of about 0.05 to about 5.0% by weight based on the total weight of the composition. Deodorant actives include antimicrobial agents such as bacteriostats and fragrances. Bacteriostats that may be used include quaternary ammonium compounds, such as cetyl-trimethylammonium bromide or cetyl pyridinium chloride, 2,4,4'-trichloro-2'-hydroxydiphenylether (Triclosan), N-(4-chlorophenyl)-N'-(3,4-dichlorophenyl)urea (Triclocarban)–, silver halides, octoxyglycerin (SensivaTm SC 50) and various zinc salts (for example, zinc ricinoleate). The bacteriostat can, illustratively, be included in the composition in an amount of 0.01–1.0% by weight, of the total weight of the composition. Triclosan, can illustratively included in an amount of from 0.05% to about 0.5% by weight, of the total weight of the composition.

Oil Phase

The oil phase of the compositions of the invention can contain the following ingredients listed below. These ingredients are also examples of liquids that may be used to produce the wet-milled active.

Cyclopentasiloxanes

Cyclomethicones, also are useful in the composition and method of the present invention and they are included in the oil phase of the present compositions. The cyclomethicones are low molecular weight, water-insoluble cyclic compounds having an average of about 3 to about 6 —[O—Si(CH$_3$)$_2$]— repeating group units per molecule and boil at atmospheric pressure in a range of from about 150 degree C. to about 250 degree C. Suitable cyclomethicones are available commercially under the tradenames SILICONE SF-1173 (octamethylcyclotetrasiloxane) and SILICONE SF-1202 (decamethylcyclopentasiloxane) from General Electric, Waterford, N.Y., and SILICONE 344 FLUID, SILICONE 245 and SILICONE 345 FLUID from Dow Corning Corporation, Midland, Mich., the tetramer being listed first in each instance. The volatile cyclic silicones can be used in combination with a linear volatile silicone, and the volatile silicones can be used in conjunction with a nonvolatile silicone or a hydrocarbon.

Silanes such as cyclopentasiloxane, cyclotetrasiloxane, or cyclohexasiloxane may also be used in compositions of the invention.

Linear Volatile or Nonvolatile Silicones

In a preferred embodiment, the volatile silicone in compositions of the invention is a low molecular weight polydimethylsiloxane having a viscosity of about 0.5 to about 5 centistokes (cs) at 25 degrees C. and a boiling point of up to about 300 degrees C. at atmospheric pressure. A low molecular weight polydimethlsiloxane having phenyl substituents also is useful in the compositions of the present invention. Furthermore, the low molecular weight polydimethylsiloxane compound can be a linear or a cyclic polydimethylsiloxane compound.

An example of a linear, low molecular weight, volatile polydimethylsiloxane compound useful in the composition and method of the present invention is hexamethyldisiloxane, available commercially under the tradename DOW CORNING 200 FLUID, from Dow Corning Corp., Midland, Mich. Hexamethyldisiloxane has a viscosity of 0.65 cs (centistokes), is highly volatile, is nongreasy, and does not leave the skin with a sticky or tacky feeling. Other linear polydimethylsiloxanes, such as decamethyltetrasiloxane, having a boiling point of about 195 degrees C., at atmospheric pressure, and a viscosity of 1.5 centistokes; octamethyltrisiloxane; and dodecamethylpentasiloxane, also are useful in the composition of the present invention. Phenyltris(trimethylsiloxy) silane can be included in the oil phase of the compositions of the invention.

Other suitable carriers for use in the composition include nonvolatile silicone materials, preferably of low viscosity, nonvolatile silicone carriers having a viscosity of less than about 500 cs, more preferably from about 5 cs to about 50cs, more preferably from about 5 cs to about 20 cs. These silicone emollients include, but are not limited to, polyalkylsiloxanes, polyalkyarylsiloxanes and polyethersiloxane copolymers. Examples of such emollients are well known in the art, some of which are described in I Cosmetics, Science and Technology 27—104 (M. Balsam and E. Sagarin ed. 1972); U.S. Pat. No. 4,202,879, issued to Shelton on May 13, 1980; and U.S. Pat. No. 5,069,897, issued to Orr on Dec. 3, 1991; which descriptions are hereby incorporated by reference.

Esters

Esters can be included in the oil phase of the compositions of the present invention. Esters which chemically, are the covalent compounds formed between acids and alcohols. Esters can be formed from almost all acids (carboxylic and inorganic) and any alcohol. Esters here are derived from carboxylic acids and an alcohol; and can be saturated or unsaturated, straight chained or branched. Specific examples include isopropyl myristate, isopropyl palmitate, isopropyl stearate, isopropyl isostearate, butyl stearate, octyl stearate, hexyl laurate, cetyl stearate, diisopropyl adipate, isodecyl oleate, diisopropyl sebacate, isostearyl lactate, C 12–15 alcohol benzoate and C18 alkyl benzoate, myreth-3 myristate, dioctyl malate, neopentyl glycol diheptanoate, neopentyl glycol dioctanoate, dipropylene glycol dibenzoate. C12-5 alcohols lactate, isohexyl decanoate, isohexyl caprate, diethylene glycol dioctanoate, octyl isononanoate, isodecyl octanoate, diethylene glycol diisononanoate, isononyl isononanoate, isostearyl isostearate, behenyl behenate, C2-, alkyl fumarate, laureth-2 benzoate, propylene glycol isoceteth-3 acetate, propylene glycol ceteth-3 acetate, octyldodecyl myristate, cetyl ricinoleate, myristyl myristate.

Hydrocarbons

The volatile or non-volatile hydrocarbons are included in the composition, either alone or in conjunction with other non-aqueous carriers. The non-volatile hydrocarbon, such as a hydrocarbon including about 10 carbon atoms to about 26 carbon atoms to avoid leaving a sticky or tacky feeling on the skin. A volatile hydrocarbon provides essentially the same benefits as the volatile silicone.

A preferred hydrocarbon is an aliphatic hydrocarbon including from about 12 to about 24 carbon atoms, and has a boiling point in the range of from about 100.degree. C. to about 300.degree. C. Exemplary volatile hydrocarbons are the commercially-available compounds such as PERMETHYL 102A, or PERMETHYL 99A and PERMETHYL 101A respectively, from Presperse, Inc., South Plainfield, N.J. Other hydrocarbons include isohexadecene, 1-decene dimer, and C.sub.13-14 isoparaffins, or paraffin wax. A hydrocarbon is useful in the gel antiperspirant composition either alone, in combination with another volatile or non-volatile hydrocarbon, or in combination with a volatile or nonvolatile silicone fluids. Some non-volatile hydrocarbon compounds are commercially available such as silkflo 344-NF and Silkflo 366-NF from Lipo Chemical INC. which are poly decene and diisooctyl cyclohexane from Henckel Corporation can be added to the oil phase too.

Emulsifiers

Emulsifiers such as silicone emulsifiers can be included in compositions of the invention. A silicone emulsifiers is mixed with oil phase first, the water phase is slowly added to the components then a water-in-oil emulsion is obtained.

The oil phase of compositions of the invention can be a blend of liquids which include a cyclosiloxane, such as cyclopentasiloxane brand named DC 245 and cyclotetrasiloxane named DC 344, cyclohexasiloxane or dimethicone DC 246. Dimethicone is available from Dow Corning under the name DC-200 fluids: hexamethyl-disiloxane, octamethyltrisiloxane, dimethicones with various viscosity, and it has a refractive index of about 1.3995., Other non-silicone liquids which can be included in the oil phase of nonlimiting of compositions of the invention include, isopropyl myristate, isopropyl palmitate, and diisopropyl sebacate. These have refractive indices respectively of 1.4340, 1.4370, 1.4320. Other nonlimiting, non-silicone oils which can be included in the oil phase of the compositions of the invention include $C_{12}$–$C_{15}$ benzoate, refractive indices 1.4798, diisopropyl adipate and octyl octanoate.

The oil phase of the compositions of the invention also includes a silicone emulsifying agent. Non-limiting examples of silicone emulsifying agents include Abil EM 90, Abil EM97 and DC 5225C. Most are the polyether substituted silicone of cyclomethiocone and dimethicone copolyol which can be obtained form Dow Corning under the name DC-5225C. This emulsifying agent is a dispersion of dimethicone and cyclomethicone copolyol, which is a silicone surfactant; in cyclomethicone (Dow Corning 245 fluid). The copolyol active is present at about 10.5% of the dispersion, and the cyclomethicone DC 245 is present at about 89.5% of the dispersion. Stable emulsions containing a large percentage of internal aqueous phase can be prepared using this emulsifying agent.

Low HLB Surfactant

Low HLB Surfactant can be included in the compositions of the invention. Such surfactants are polyglyceryl-3 diisostearate, polyglyceryl-2 diisostearate, glycryl isosterate or gyceryloleate etc. The HLB for these surfactants is usually less than 8.

The AP or deodorant active is present in the aqueous phase at usually about 1% to about 50% of the total composition, more preferably about 1% to about 40% of the total composition, still more preferably about 1% to about 30% of the total composition.

Optional Ingredients

Compositions of the invention can further comprise other cosmetic ingredients such as fragrances, colorants, emollients, preservatives, and thickeners.

EXAMPLES

The following are specific examples of the compositions of the invention which have been made.

As noted above, antiperspirant active powders that have been milled in the presence of liquids are referred to in this specification as wet-milled. Antiperspirant active powders that have been milled in the in air are referred to in this specification as dry-milled. A wet-milled product that has been used in compositions of the invention is made by Giulini Corporation, Ludwigshaven, Germany: The Product is called S450GLY.

A wet-milled product that has been used in compositions of the invention is made by Reheis, Inc, Berkeley Heights, N.J.: The product is called Reach AZP-908 gel.

Formulation Example

Soft Solid

| Raw Material | Formulation A, weight % (invention) | Formulation B, weight % |
|---|---|---|
| Cyclomethicone | 34.75 | 57.75 |
| Dimethicone | 8.00 | 8.00 |
| Microcrystaline wax | 1.75 | 3.50 |
| Syncrowax HGL-C | 1.75 | 3.50 |
| Silicone Dioxide | 0.75 | 0.75 |
| AZG (Traditional) | 0.00 | 26.50 |
| AZG (Wet-milled), 50% active | 53.00 | 0.00 |

Formulation A, utilizing wet-milled active, exhibits similar or slightly improved stability to Formulation B, which uses traditional anhydrous salts. Formulation A does this with significantly less suspending/gelling agents.

Soft Solids

Formulation A & B

1. Heat Cyclomethicone, Dimethicone and waxes to 180 F. while mixing at moderate speed.
2. Stop heating at 180 F., Let it cool to 170 F. and add Silicone Dioxide and Mix at high speed till the phase become homogeneous.
3. Add wett-miled AZG and increase the mixing speed.
4. At 140 F. pour the product in the containers and let it set.

Formulation Example

Roll-on

| Raw Material | Formulation C, weight % (invention) | Formulation D, weight % |
|---|---|---|
| Cyclomethicone | 45.43 | 67.43 |
| Quaternium-18 Bentonite | 2.25 | 2.25 |
| Propylene Carbonate | 0.75 | 0.75 |
| Dioctyl Adipate | 5.00 | 5.00 |
| Silicone Dioxide | 0.25 | 0.25 |
| Glycerine | 2.00 | 2.00 |
| Antioxidant | 0.02 | 0.02 |
| Fragrance Oil | 0.30 | 0.30 |
| AZG (Traditional) | 0.00 | 22.00 |
| AZG (Wet-milled), 50% active | 44.00 | 0.00 |

The wet-milled active in Roll-on Formulation C shows superior suspending properties resulting in a very insignificant phase separation. Formulation D displays 15% phase separation versus 3% observed in Formulation C after 48 hours. It was also discovered that Formulation C exhibits significantly less whitening on the skin.

Roll-on

Formulation C & D

1. Mix Cyclometicone, Dioctyl Adipate and slowly disperse Quaternium-18 Bentonite.

2. When Bentonite is dispersed, add Silicone Dioxide and Propylene Carbonte. Mix for 30 minutes.
3. Add. glycerine, antioxidant and the AZG, Mix for 30 minutes and then homogenize at high speed for 30 minutes.
4. Add the fragrance and mix.
5. Pour in the desired containers.

Formulation Example

Solid Stick

| Raw Material | Formulation E weight % | Formulation F weight % (invention) |
|---|---|---|
| Cyclomethicone | 40.7 | 16.7 |
| PPG - 14 Butyl Eather | 17.5 | 17.5 |
| Stearyl Alcohol | 13.0 | 13.0 |
| PEG - 8 Distearate | 2.0 | 2.0 |
| Talc | 2.0 | 2.0 |
| AZG (Powder) | 24.0 | 0 |
| AZG (Wet - Milled) | 0 | 48.0 |
| Perfume | 0.8 | 0.8 |

Formulation E Containing traditional anhydrous AZG salt (Powder), Exhibits poor Physical stability at elevated temperature (120 F.) as compared to formulation F with Wet—Milled active (AZG salt).

AP Solid Stick (Formulation E & F)

1. Heat cyclomethicone, PPG-14Butyl ether, Stearyl alcohol and PEG-8 Distearate to 180 F.
2. Keep mixing the batch until no particles are visible.
3. At 170 F. add Talc, mix well, and then start adding the AZG while mixing at high speed.
4. At 140 F., pour the product in suitable containers.

While particular embodiments of the invention have been shown and described, various modifications will be apparent to those skilled in the art, and therefore it is not intended that the invention be limited to the disclosed embodiments or the details thereof, and departures may be made therefrom within the spirit and the scope of the inventions.

What is claimed is:

1. An antiperspirant composition which comprises:
   a) a wet-milled antiperspirant active material;
   b) a silicone and/or hydrocarbon carrier material; and
   c) a suspending agent or gellant, other than Al—Mg-hydroxystearate or cylco-methicone and dimethicone cross-polymer.
2. An antiperspirant composition according to claim 1, characterised in that the suspending agent or gellant is a gellant.
3. An antiperspirant composition according to claim 2, characterised in that the gellant comprises a wax.
4. An antiperspirant composition according to claim 3, characterised in that the wax comprises a microcrystalline wax.
5. An antiperspirant composition according to claim 1, characterised in that the suspending agent or gellant is a suspending agent.
6. An antiperspirant composition according to claim 5, characterised in that the suspending agent comprises quaternium-18 bentonite.
7. An antiperspirant composition according to claim 2, characterised in that the gellant comprises a fatty alcohol.
8. An antiperspirant composition according to claim 7, characterised in that the fatty alcohol comprises stearyl alcohol.
9. An antiperspirant composition according to claim 1, characterised in that the wet-milled antiperspirant active material is 50% wet-milled AZG.
10. An antiperspirant composition according to claim 1, which is in the form of a solid stick.
11. An antiperspirant composition according to claim 1, which is in the form of a soft solid.
12. An antiperspirant composition according to claim 1, which is in the form of a roll-on.
13. A method for improving the stability of an antiperspirant product comprising the use of an antiperspirant composition according to claim 1.
14. A method for treating human body odour, comprising the topical application of an antiperspirant composition according to claim 1.
15. An antiperspirant composition according to claim 1 which comprises:
   (a) 20 to 50% of said wet milled antiperspirant active material:
   (b) 5 to 50% of said silicone and/or hydrocarbon carrier material.
16. An antiperspirant composition which comprises:
   a) a wet-milled antiperspirant active material;
   b) a silicone and/or hydrocarbon carrier material.
17. An antiperspirant composition according to claim 16, which is in the form of a solid stick.
18. An antiperspirant composition according to claim 16, which is in the form of a soft solid.
19. An antiperspirant composition according to claim 16, which is in the form of a roll-on.
20. A method for reducing the tendency of antiperspirant products to leave white marks on the skin and on the clothes of the consumer, said method comprising the use of an antiperspirant composition according to claim 16.

* * * * *